(12) United States Patent
Prutchi

(10) Patent No.: US 6,662,055 B1
(45) Date of Patent: Dec. 9, 2003

(54) MULTI-ELECTRODE INTRAVASCULAR LEAD

(75) Inventor: David Prutchi, Lake Jackson, TX (US)

(73) Assignee: Impulse Dynamics NV, Curacao (AN)

( * ) Notice: Subject to any disclaimer, the term of this patent is extended or adjusted under 35 U.S.C. 154(b) by 0 days.

(21) Appl. No.: 09/459,289

(22) Filed: Dec. 17, 1999

(51) Int. Cl.[7] ............................................. A61N 1/36
(52) U.S. Cl. ...................................................... 607/122
(58) Field of Search ................................. 607/119, 122, 607/123; 600/373, 374, 381

(56) References Cited

U.S. PATENT DOCUMENTS

| | | | | |
|---|---|---|---|---|
| 4,484,586 A | * | 11/1984 | McMickle et al. | 128/786 |
| 5,246,014 A | * | 9/1993 | Williams et al. | 607/122 |
| 5,330,521 A | * | 7/1994 | Cohen | 607/122 |
| 5,755,766 A | * | 5/1998 | Chastain et al. | 607/122 |
| 5,796,044 A | * | 8/1998 | Cobian et al. | 174/103 |

* cited by examiner

Primary Examiner—Jeffrey R. Jastrzab
Assistant Examiner—Frances P. Oropeza
(74) Attorney, Agent, or Firm—Reed Smith LLP; William H. Dippert

(57) ABSTRACT

An intravascular lead having a distal and proximal ends, comprising at least one electrode electrically connected to a conductive insulated wire of a predetermined diameter, tapered at least at one predetermined location along said wire towards its distal end to provide a predetermined smaller diameter wire, thus presenting a main proximal relatively thick lead segment, and a relatively thinner distal lead segment, allowing catheterization of the cardiac sinus and in particular the delivery of said electrode into a selected coronary venule.

17 Claims, 5 Drawing Sheets

MULTI-ELECTRODE INTRAVASCULAR LEAD

FIELD OF THE INVENTION

The present invention relates to chronically-implantable electrical leads for intravascular delivery of electrodes. More particularly it relates to a multi-electrode intravascular lead, designed for use in coronary veins and venules.

BACKGROUND OF THE INVENTION

Chronically-implantable leads for intravascular delivery of electrodes to be positioned in the coronary veins must be of small diameter (typical dimension <4 French), to enable effective catheterization of the Smaller venules. In addition, leads for intravascular or intracardiac chronic implants must be flexible enough to withstand the harsh cyclic loading conditions to which they are exposed. For this reason, these leads are usually constructed with one or more wire coils that impart the lead its desirable mechanical properties. For the purpose of electrically controlling the cardiac muscle, as described by Ben-Haim et al. (PCT/IL97/00012) leads must present low resistance (or low impedance in AC systems) to electric currents in order to be effective. Resistance however is a function of material properties (bulk resistivity), cross-section of the conductor and the conductor's length. As such, the long, thin wires needed for the construction of very thin leads, and that results in high resistance values, which are highly inefficient for their use with implantable electrical muscle controllers.

For example, prior art 20 cm long, 3 to 4 French wide tetrapolar leads, having MP35N coated wires, forming parallel coils have terminal-to-electrode resistance values ranging from 150 Ohms to 200 Ohms. At the same time, typical electrodes for electrical muscle control have ionic conduction impedances of approximately 150 Ohms. As such, the wire resistance accounts for energy loss of as much as half the energy that could otherwise be delivered to the tissue.

Multipolar leads for permanent implant in the coronary veins are well known and are in current use for left-ventricular pacing. Daubert et al. (J. C. Daubert, P. Ritter, H. LeBreton, D. Gras, C. Leclercq, A. Lazarus, J. Mugica, P. Mabo and S. Cazeau, "Permanent left-ventricular pacing with transvenous leads inserted into the coronary veins", PACE, 21(1-ll), 239–245, 1998) describe clinical trials that had been conducted using a specially-developed coronary-sinus lead for this purpose.

Furthermore, thin catheters for acute catheterization are commercially available. These catheters usually use parallel-cables (not coiled) to achieve a small cross-section. However parallel-cable technology for chronically-implantable leads is still under development, since leads constructed in this technology may not be as robust and durable as those made using wire coils, and therefore require careful design to achieve the required reliability. Moreover, these leads do not have an intrinsic lumen for a guidwire or stylet, and thus require the development of new positioning techniques.

The closest geometrical configuration related to the present invention of which the inventor is aware is described in U.S. Pat. No. 5,755,766 (Chastain et al.). Named "Open-ended Intravenous Cardiac Lead", that patent discloses a lead which has a narrower distal end than the rest of the lead body. However, the change in the lead diameter is caused by the reduction in the lumen diameter, bringing no electrical or structural improvements to the design of the lead.

Furthermore, in that patent there is a thin lead extension, which is deployable after the lead had been positioned. However, the lead extension of the lead described therein carries electrodes through conductors which maintain their diameter along the length of the catheter and must fit within the lumen of the lead (this may prove impractical, even for high impedance connections). Again, this option neither reduces the electrical resistance of the lead, nor does it improve the overall reliability of the lead.

To-date leads are built using conductors of constant-diameter. As such, the resistivity is constant along the lead. In contrast to that, in the present invention resistivity is maintained low along most of the lead, only increasing at the distal end, where reduced diameter lead is required to effectively catheterize the coronary sinus and coronary veins.

BRIEF DESCRIPTION OF THE INVENTION

It is the object of the present invention to provide an improved intravascular lead for the delivery of electrodes suitable for use in coronary veins.

It is another object of the present invention to provide an intravascular lead that is relatively thinner at its distal end in its diameter with respect to known intravascular leads, thus allowing insertion of the distal end of the lead and delivering of an electrode in thinner coronary venules.

Yet another object of the present invention is to provide such an intravascular lead constructed at its distal end of tapered coated cables, thus imparting lower impedance and smaller diameter intravascular lead end than prior art intravascular leads.

There is thus provided, with accordance with a preferred embodiment of the present invention, an intravascular lead comprising a at least one electrode electrically connected to a conductive wire of a predetermined diameter, tapered at least at one predetermined location along said wire towards its distal end to provide a predetermined smaller diameter wire, thus presenting a main proximal relatively thick lead segment, and a relatively thinner distal lead segment, allowing catheterization of the cardiac sinus and in particular the delivery of said electrode into a selected coronary venule.

The tapering of the end of the wire renders the lead lower total impedance relatively to other prior-art leads.

BRIEF DESCRIPTION OF THE FIGURES

In order to better understand and appreciate the present invention a detailed description of the invention is provided below, with reference to the attached Figures, in which.

DETAILED DESCRIPTION OF THE INVENTION AND FIGURES

Figure 1:
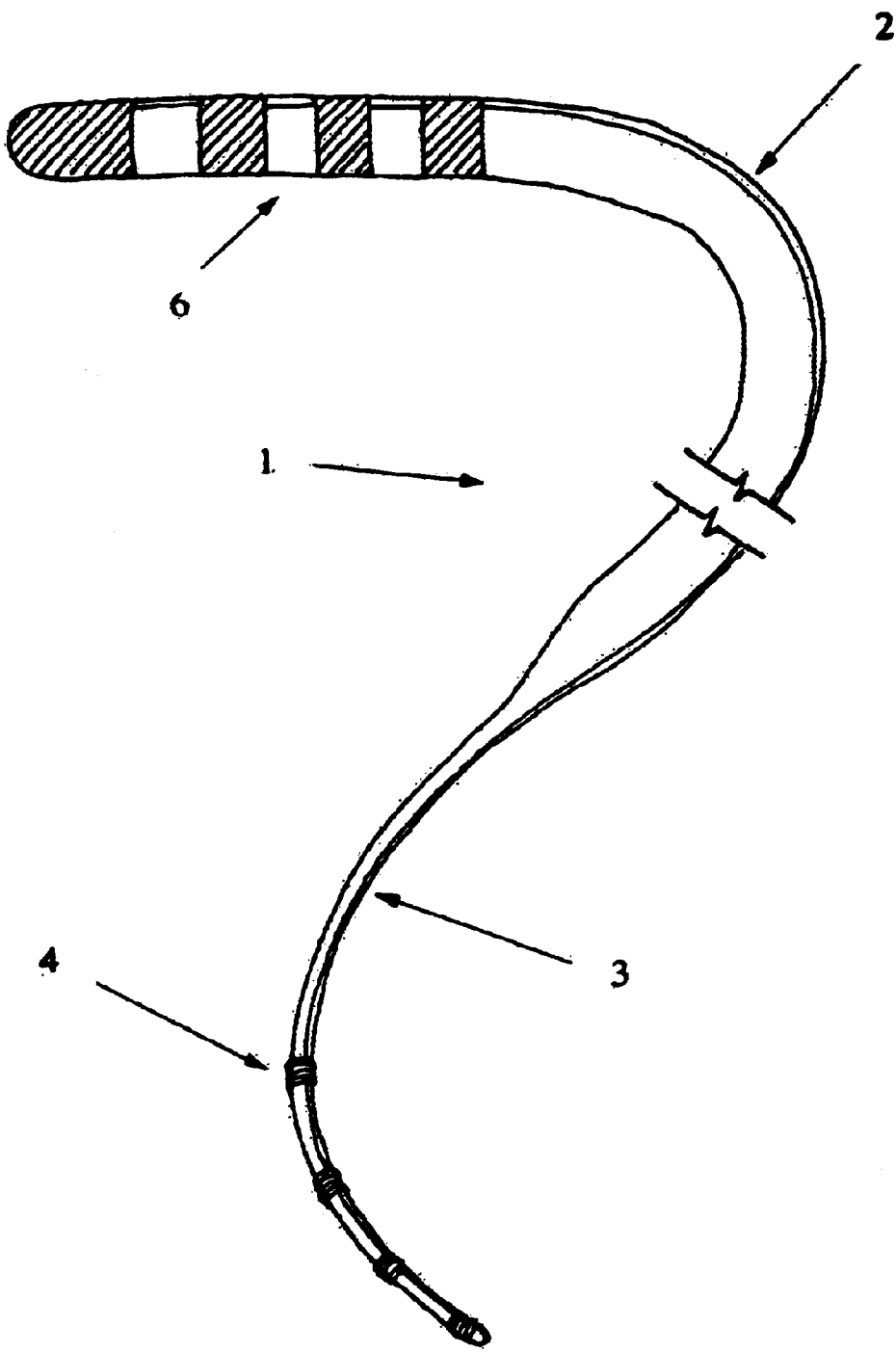
FIG. 1 illustrates a general view of a typical embodiment of the multi-electrode low-impedance intravascular lead of the present invention (a tetrapolar lead).

FIG. 1 illustrates a general view of a typical embodiment of the multi-electrode low-impedance intravascular lead of the present invention. The lead (assigned the general reference numeral 1) comprises a low-impedance thick lead segment (2) provided with a four-connections connector (6) at its proximal end, and a high-impedance thin lead segment (3) towards the distal end of the lead, with a four electrode array (4). The thin segment length is predetermined by the length required in the catheterization of the cardiac sinus and cardiac venules. As shown, the lead segment (2) is thick (and thus can be made to have low resistance) along most of its length, but has a thinner segment (3) towards its distal end, allowing for more ease and convenience with the catheterization of the coronary sinus and cardiac veins.

Figure 2:
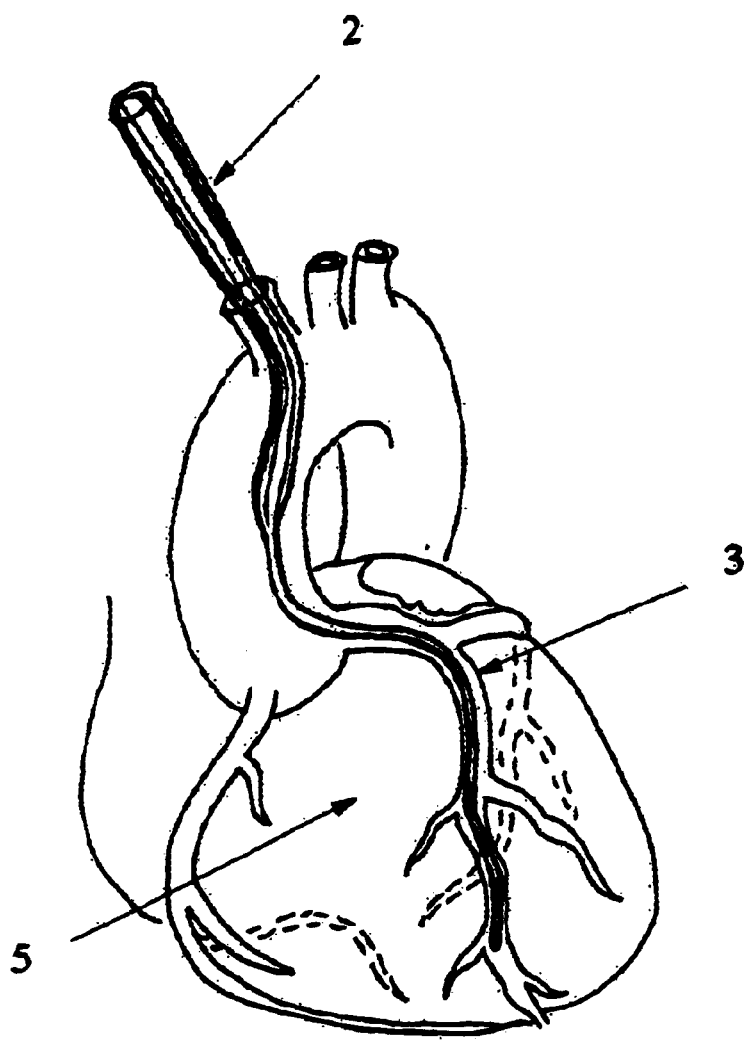
FIG. 2 demonstrates the use of the same typical embodiment of the present invention in cardiac coronary veins.

FIG. 2 illustrates the use of the same typical embodiment of the present invention in cardiac coronary veins. As shown, the thick segment (2) typically having a diameter of 6 to 8 French, of the lead extends from the implantable device all the way down the vein to the right atrium (5). This thick lead segment (2) may have a length of 30 to 40 cm to enable appropriate positioning of the implantable device, as well as sufficient "slack" to accommodate displacement, rotation and growth without subsequent dislocation of the electrodes from their predetermined position. On the other hand, the thin, distal segment (3) may have a length of only 5 to 10 cm to enable catheterization of the coronary veins.

The unique configuration of the multi-electrode intravascular lead of the present invention makes it easier to be navigated through the coronary sinus and permanently located in the coronary venule of choice. At the same time, this makes it possible to have a lead with connector-to-electrode resistance of only a few tens of Ohms. For example, the thick segment can be manufactured to pose a resistance of 5 to 20 Ohms (say 15 Ohms), while the short, thin segment may add an additional resistance of 10 to 40 Ohms adding up to a total connector-to-electrode impedance of 15 to 60 Ohms (a 5 to 10-fold improvement over the prior art devices).

Figure 3:
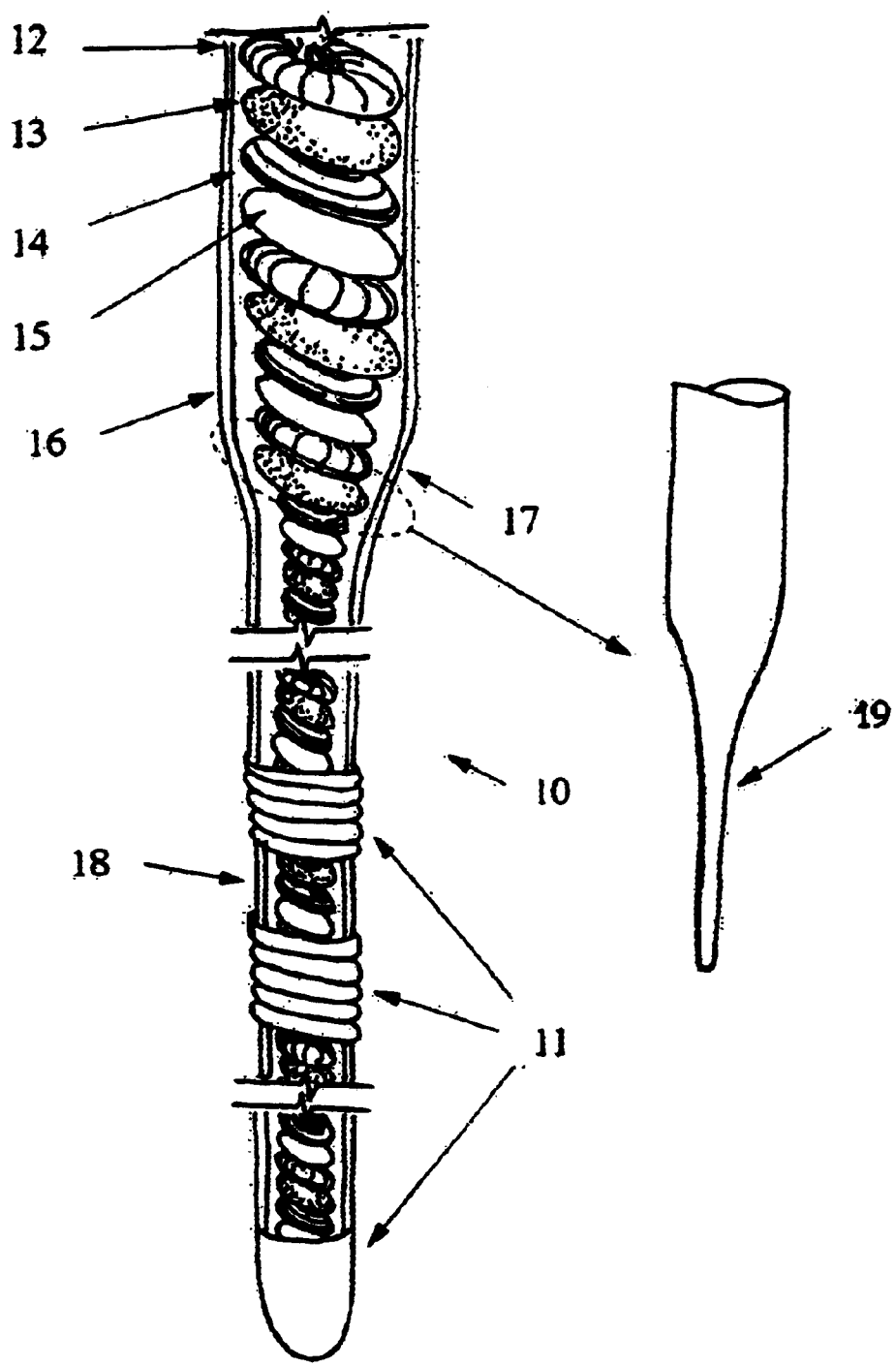
FIG. 3 depicts a see-through view of the distal end of same typical embodiment of the low-impedance intravascular lead of the present invention.

FIG. 3 shows the construction detail of a preferred embodiment of the multi-electrode low-impedance intravascular lead of the present invention.

Shown is a tetrapolar intravascular lead (generally referenced by the numeral 10), constructed in accordance with the present invention, comprising four coated insulated electrically conductive wires (12–15), coiled parallely (along a substantial portion of the lead), externally covered by an insulating jacket (16). At a transition area (17), the wires (12–15), still coiled parallely, become narrower, thus the whole lead diameter decreases, to present a thinner distal end segment (18). At the point at which it is desirable to reduce the lead diameter, the cross-section of the wires forming the parallel coils is gradually reduced. Typically, the reduction in the wire cross-section area would be in the range of 30 to 70 per cent from the original thick segment cross-section area. This is achieved by the use of tapered wires (19), one of which is depicted in FIG. 3A, shown magnified. As this happens, the outer diameter of the coils is also reduced, but at the same time, a lumen of substantially constant diameter is retained, making it possible to use the standard or tapered stylets to aid the implant and positioning of the lead. At the distal end there is an array of electrodes (11)

Figure 4:
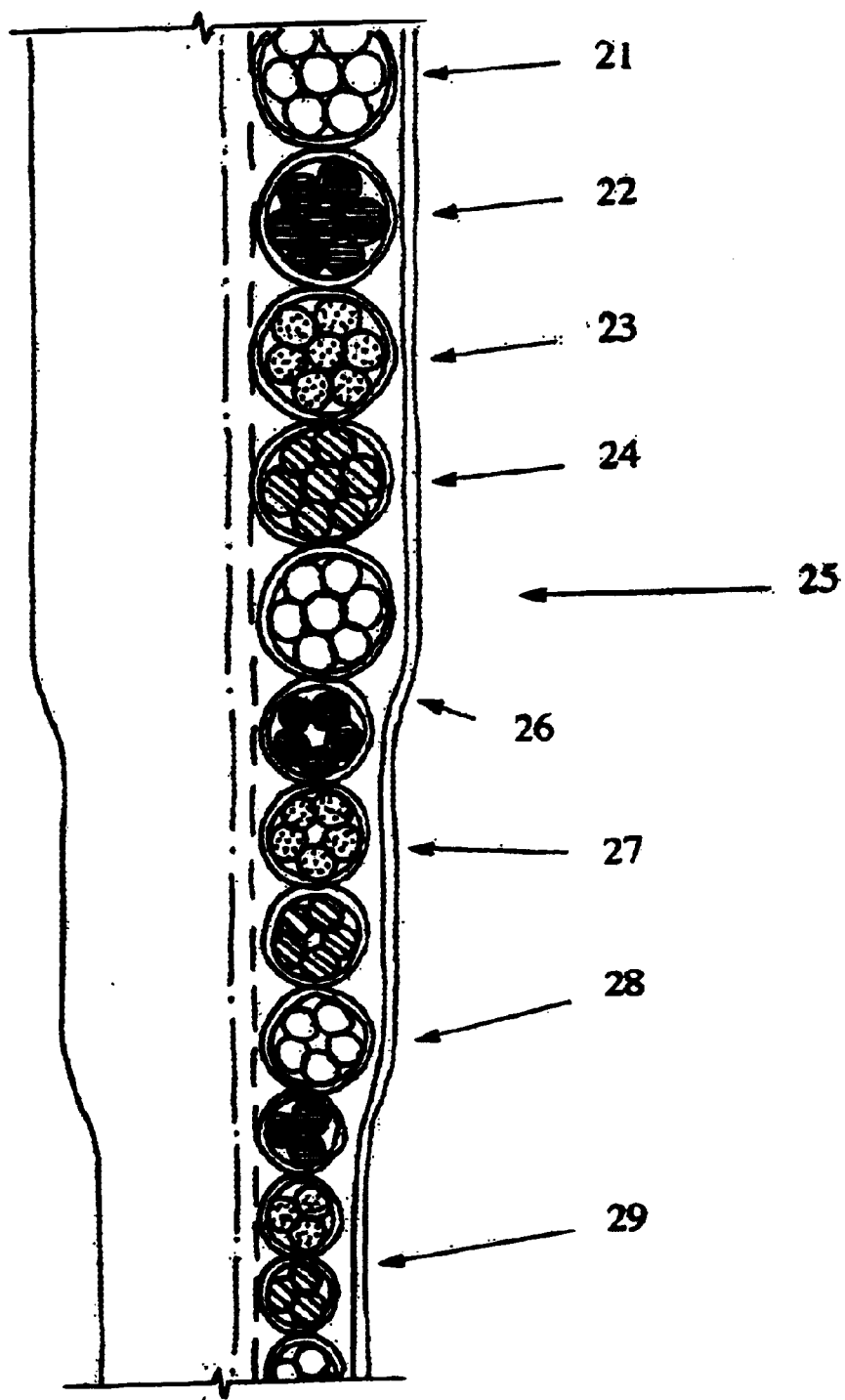
FIG. 4 is a detailed view of longitudinal cross-section across the narrowing section of the low-impedance intravascular lead of the present invention, near its distal end.

Although the use of a gradually-tapered wire is the preferred method of construction, other techniques can be equally applied in order to provide a narrowing wire. As shown in FIG. 4, if filament cables (21–24) are used as the lead constructors, then the tapering can be done discretely, by reducing the number of filaments in the wire within the transition area of the wire. At the thick segment of the lead (25), the cable is constructed of 7 filament wires. At a predetermined transitional location (26) the cables became thinner due to reduction in the number of filament wires used—in this case 5 wires (27). Optionally, the lead can be further tapered at a second transition location (28), where the cables become narrower as the number of filament wires is reduced to 3 (29).

Figure 5:
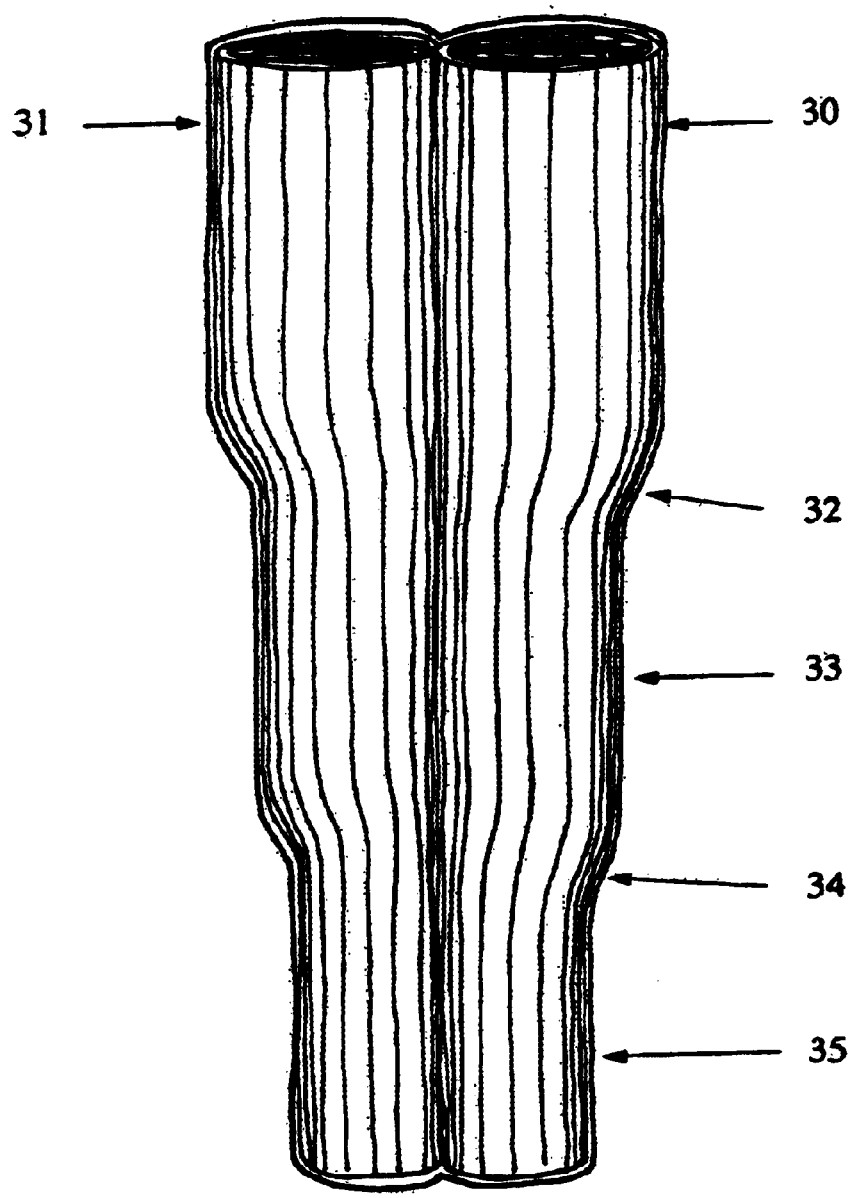
FIG. 5 is a longitudinal cross-section view of another embodiment of the multi-electrode intravascular lead of the present invention, having a varying diameter distal end.

The filament cable can be constructed of coiled filament wires but also of straight parallel wires, since the same technique can be applied to form a tapered lead using parallel-cable technology. An example of how the invention applies to the development of parallel-cable leads is shown in FIG. 5., where another typical embodiment of the lead of the present invention is constructed of two parallel coated cables (30, 31). Each of the cable is tapered at a predetermined transition location (32) preferably same for both cables, to present a narrower segment (33)—in this example the number of filament wires is reduced to achieve the narrower segment. At a second transitional location (34) is optionally provided where the lead is further tapered to yet narrower segment (35).

The advantages of the lead of the present invention are very large over the prior art leads when applied to the design of leads for Electrical Muscle Control, cardioversion, defibrililation or other applications where it is desirable to apply large electrical currents to zones of the heart by way of the coronary venules.

For example, a 30 mA (initial current) pulse applied as described by Ben-Haim et al. (PCT/IL97/00012) would require an initial driving voltage of approximately 18 V using a prior art bipolar lead, that yields a combined lead-resistance/ionic-conductance impedance of 600 Ohms. In contrast, only 6 V would be needed, using a lead constructed in a conservative manner, according to the present invention. In this same example, and considering an implantable muscle controller where the energy delivered to the tissue comes from the discharge of a tank capacitor, prior-art leads would consume 112.5% more energy than a lead constructed in accordance with the present invention.

Other applications for the disclosed lead and methods of its construction of the present invention may be found, especially those related to the delivery or acquisition of signals from tissues or organs that can be accessed only through thin catheters.

It should be clear that the description of the embodiments and attached Figures set forth in this specification serves only for a better understanding of the invention, without limiting its scope as covered by the following Claims.

It should also be clear that a person skilled in the art after reading the present specification could make adjustments or amendments to the attached Figures and above described embodiments that would still be covered by the following Claims.

I claim:

1. An intravascular electrode lead having a proximal end and a distal segment and comprising at least one of a plurality of electrodes, each of said at least one of a plurality of electrodes electrically connected to a conductive insulated wire of a predetermined diameter and having a proximal end and a distal end, the wire tapered at least at one predetermined location along its length towards the distal end so as to present a thinner wire, thus obtaining a tapering multi-electrode lead having a main proximal relatively thick lead segment, and a relatively thin distal lead segment, allowing catheterization of the cardiac sinus and the delivery of said electrode into a selected coronary venule, wherein a lumen of substantially constant diameter is retained through the lead making it possible to use a standard or tapered stylet in order to aid implantation and positioning of the lead.

2. The intravascular electrode lead according to claim 1, wherein four insulating electrically conductive wires are used in the construction of the lead.

3. The intravascular electrode lead according to claim 1, wherein a four-connections electrical connector is provided at its proximal end.

4. The intravascular electrode lead according to claim 1, wherein said distal segment of said lead is provided with a four-electrode array.

5. The intravascular electrode lead according to claim 1, wherein the relatively thin distal lead segment has a predetermined length long enough for the catheterization of the coronary sinus and cardiac venules.

6. The intravascular electrode lead according to claim 1, wherein the relatively thin distal lead segment and the relatively thick lead segment each have a cross-sectional area and the cross-sectional area of the relatively thin distal lead segment is from about 30 to 70 percent of the cross-sectional area of the relatively thick lead segment.

7. The intravascular electrode lead according to claim 1, wherein the relatively thick lead segment has a diameter of from 6 to 8 French.

8. The intravascular electrode lead according to claim 1, wherein said relatively thick lead segment has a length of from 30 to 40 cm.

9. The intravascular electrode lead according to claim 1, wherein said relatively thin distal lead segment has a length of from 5 to 10 cm.

10. The intravascular electrode lead according to claim 1, wherein said relatively thick lead segment poses a resistance of from 5 to 20 Ohms.

11. The intravascular electrode lead according to claim 1, wherein said distal relatively thin lead segment poses a resistance of from 10 to 40 Ohms.

12. The intravascular electrode lead according to claim 1, wherein the lead has a total impedance of from 15 to 60 Ohms.

13. The intravascular electrode lead according to claim 1, wherein said conductive insulative wire is coiled along a portion of the lead.

14. The intravascular electrode lead according to claim 1, wherein the wire is externally covered by an insulating jacket.

15. The intravascular electrode lead according to claim 1, wherein said tapering of the lead is achieved by a gradual reduction of the diameter of the wire used in the construction of the lead at a predetermined transition location on said wire.

16. The intravascular electrode lead according to claim 1, wherein the wire is formed from filaments, and wherein at a predetermined location along said wire, the number of filament wires forming said wire is reduced.

17. The intravascular electrode lead according to claim 1, wherein said wire is tapered in several locations along said lead.

* * * * *